(12) United States Patent
Srinivasan et al.

(10) Patent No.: US 8,047,991 B2
(45) Date of Patent: Nov. 1, 2011

(54) AUTOMATIC IDENTIFICATION OF ORIENTATION IN MEDICAL DIAGNOSTIC ULTRASOUND

(75) Inventors: Seshadri Srinivasan, Mountain View, CA (US); Bimba Rao, San Jose, CA (US); Ismayil Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 710 days.

(21) Appl. No.: 11/505,560

(22) Filed: Aug. 16, 2006

(65) Prior Publication Data

US 2008/0097212 A1   Apr. 24, 2008
US 2009/0227871 A2   Sep. 10, 2009

(51) Int. Cl.
*A61B 8/00* (2006.01)

(52) U.S. Cl. ........ 600/443; 600/447; 600/453; 600/455; 600/437; 600/454

(58) Field of Classification Search .................. None
See application file for complete search history.

(56) References Cited

U.S. PATENT DOCUMENTS

| | | | |
|---|---|---|---|
| 5,454,372 A | 10/1995 | Banjanin et al. | |
| 5,622,173 A | 4/1997 | Bisson et al. | |
| 5,690,116 A * | 11/1997 | Goujon | 600/454 |
| 5,782,769 A | 7/1998 | Hwang et al. | |
| 5,910,119 A | 6/1999 | Lin | |
| 6,017,309 A | 1/2000 | Washburn et al. | |
| 6,030,044 A | 2/2000 | Kosugi et al. | |
| 6,068,598 A * | 5/2000 | Pan et al. | 600/453 |
| 6,071,241 A | 6/2000 | Washburn et al. | |
| 6,126,605 A | 10/2000 | Washburn et al. | |
| 6,162,176 A | 12/2000 | Washburn et al. | |
| 6,176,830 B1 | 1/2001 | Freiburger | |
| 6,322,509 B1 * | 11/2001 | Pan et al. | 600/443 |
| 6,350,241 B1 | 2/2002 | Lifshitz | |
| 6,500,125 B1 | 12/2002 | Muzilla et al. | |
| 6,520,915 B1 | 2/2003 | Lin et al. | |
| 6,663,567 B2 | 12/2003 | Ji et al. | |
| 6,760,486 B1 | 7/2004 | Chiao et al. | |

OTHER PUBLICATIONS

U.S. Appl. No. 11/241,603, filed Sep. 29, 2005.

* cited by examiner

*Primary Examiner* — Unsu Jung
*Assistant Examiner* — Nigel Fontenot

(57) ABSTRACT

Orientation is automatically identified in medical diagnostic ultrasound image. An area or volume based process, such as region shrinking or using locations associated with flow or tissue structure, determines a direction or orientation. Real-time imaging in B-mode and/or flow mode may be enhanced based on the direction or orientation.

20 Claims, 2 Drawing Sheets

AUTOMATIC IDENTIFICATION OF ORIENTATION IN MEDICAL DIAGNOSTIC ULTRASOUND

BACKGROUND

The present embodiments relate to identification of orientation. In particular, orientation of flow or structure is determined for medical diagnostic ultrasound imaging.

Medical diagnostic ultrasound imaging may be used to show flow with respect to tissue, such as flow mode image overlaid with a B-mode image. B-mode data determines whether a given location is associated with tissue or with flow. A B-mode value above a threshold indicates a location associated with tissue. Color bleed from flow data over vessel walls represented by B-mode data occurs since B-mode amplitude alone may not be an adequate identifier of vessel walls. At low velocity scales, significant flash may occur in flow imaging, since B-mode amplitude may not sufficiently identify valid tissue and anatomical structures. Further thresholding may be provided, such as removing flow information below a velocity and/or energy threshold. Removal may create holes in the flow representation.

The B-mode and flow mode data are acquired along a plurality of scan lines. For flow mode, velocity information represents motion along the scan lines. Depending on the location of the structure scanned, the flow may not be only along the scan lines. The velocity information may be inaccurate since flow perpendicular to the scan line may not be detected.

BRIEF SUMMARY

By way of introduction, the preferred embodiments described below include methods, systems and computer readable media for automatic identification of orientation in medical diagnostic ultrasound. An area or volume based process, such as region shrinking or processing locations associated with flow or tissue structure, determines a direction or orientation. Real-time imaging in B-mode and/or flow mode may be enhanced based on the direction or orientation.

In a first aspect, a method is provided for automatic identification of orientation in medical diagnostic ultrasound. Ultrasound data representing flow in a region of a tissue structure is obtained. Locations associated with the region are determined as a function of the ultrasound data representing flow. An orientation of the tissue structure is determined as a function of the locations.

In a second aspect, a computer readable storage medium has stored therein data representing instructions executable by a programmed processor for automatic identification of orientation in medical diagnostic ultrasound. The storage medium includes instructions for: obtaining ultrasound data representing flow in a region; region shrinking as a function of the ultrasound data representing flow; and determining a flow direction as a function of the region shrinking.

In a third aspect, a system is provided for automatic identification of orientation in medical diagnostic ultrasound. A memory is operable to store ultrasound data comprising velocity data, energy data or both. A processor is operable to apply an area or volume based process to the ultrasound data. The processor is operable to identify a line as a function of the area or volume based process and free of a determination of a location of maximum velocity, energy or both.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Area- or volume-based image enhancement is applied to color flow and/or B-mode images. Area-based processing, such as morphological processing, on B-mode and/or flow images identifies an orientation of flow or tissue structure (e.g., vessel walls). The orientation information may be used to a) reduce artifacts in color flow imaging, such as holes, bleed and flash, b) automatically correct velocities, c) steer scan-lines, d) automatically identify a spectral Doppler window position, orientation and size, and/or e) enhance B-mode and/or flow mode images. The identification of a direction allows adaptive filtering of the B-mode images.

Figure 1:
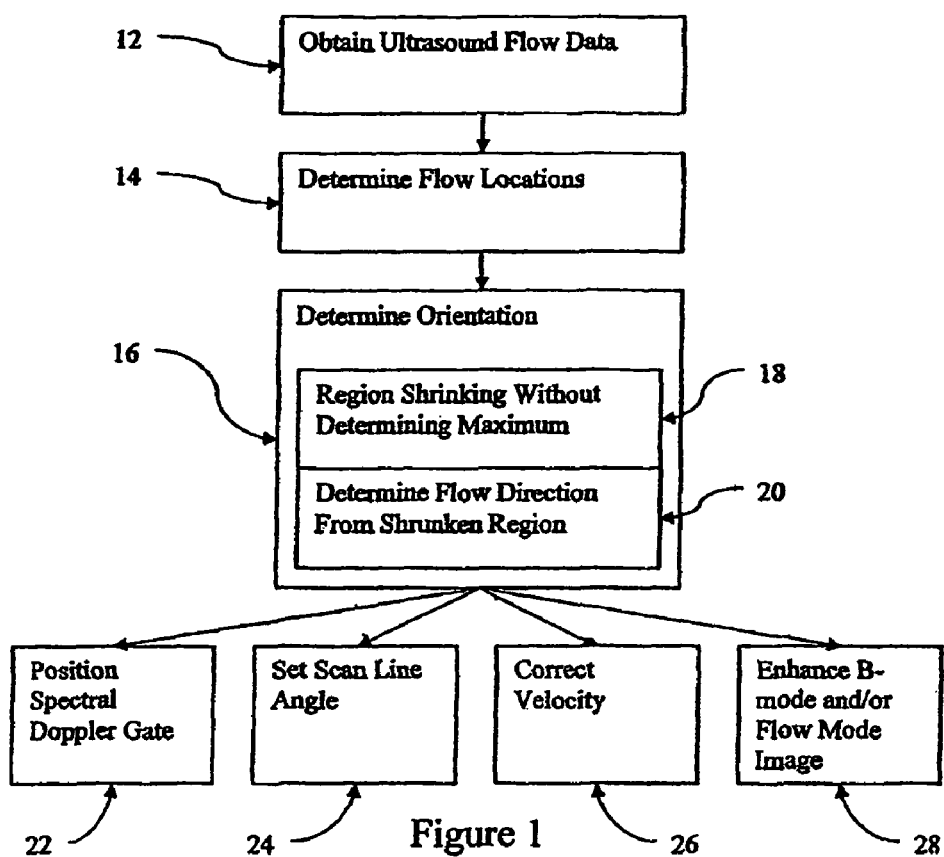
FIG. 1 is a flow chart diagram of one embodiment of a method for automatic identification of orientation in medical diagnostic ultrasound.

FIG. 1 shows a method for automatic identification of orientation in medical diagnostic ultrasound. The method is implemented by a medical diagnostic ultrasound imaging system, a review station, a workstation, a computer, a PACS station, a server, combinations thereof, or other device for image processing ultrasound data. For example, the system or computer readable media shown in FIG. 3 implements the method. The method is implemented in the order shown or a different order. Additional, different, or fewer acts may be performed. For example, acts 22, 24, 26 and 28 are optional. As another example, act 16 is performed without acts 14, 18 and/or 20. In another example, act 14 is performed without acts 16, 18 and/or 20.

In act 12, ultrasound data is obtained. The ultrasound data is obtained during real-time imaging, such as obtaining data as a patient is scanned. Alternatively, the ultrasound data is obtained from a memory, such as obtaining the data from a database of images, a patient record or a transfer from another device. The ultrasound data is formatted for display on a display device or in another format, such as a Polar coordinate or other acquisition format. The data is obtained by requesting the data, loading the data, receiving the data, recording the data, or other process.

The ultrasound data represents flow in a region. For example, the data is velocity values, energy values, variance values or combinations thereof. Other Doppler or flow information may be used, such as motion information determined from correlation of B-mode data.

The region corresponds to a blood pool, vessel, artery, other cardiovascular structure, or other fluid containing structure. In an organ, flow of vessels and veins may perfuse the organ. The region may be associated with the digestive system or other systems. The region is two or three dimensional, such as an area or a volume. Other regions may be used. The ultrasound data includes samples of the area or volume along any regular or irregular grid.

Data associated with tissue structure with or without flow may be obtained. For example, B-mode data representing tissue structures containing flow is obtained. The tissue structures may be vessel walls, organ tissue or other structures. The region represented by the obtained data includes only flow information or flow and tissue information.

The ultrasound data is obtained without processing, such as raw data output by a receive beamformer. Some processing may be provided, such as receiving data output by a detector or estimator without further processing. Alternatively, the ultrasound data is processed, such as spatially or temporally filtered.

In one embodiment, bleed of the ultrasound data representing flow onto locations associated with tissue boundaries is suppressed or reduced. Due to resolution differences, flow data (e.g., velocity or energy) may overlay desired tissue data at boundaries, such as a vessel wall. Any function may be used to reduce the color (i.e., flow) artifact. The bleed may be suppressed as a function of B-mode information. An enhanced B-mode image ($B_{enh}$) (e.g., speckle reduced B-mode image) and an edge image ($B_{edge}$) are computed. In one embodiment, the enhanced B-mode image is formed by any speckle reduction process, such as frequency or spatial filtering. Alternatively, the raw B-mode image is used for the enhanced B-mode image. The edge image is a gradient image of the B-mode data. For example, the edge image is determined as $B_{edge}=[B(i,j)-B(i,j-1)]/2+[B(i,j)-B(i-1,j)]/2$, where $B(i,j)$ is the B-mode data.

Spatial locations which should not include flow information are identified from the enhanced and edge images. A threshold, $Edge_{th}$ is applied to the edge image, $B_{edge}$, and another threshold, a B-mode dominance threshold ($B_{th}$), is applied to the enhanced B-mode image, $B_{enh}$. Where the B-mode information exceeds the threshold of either test, the flow information is set to zero to suppress bleed (e.g., if $B_{edge}<Edge_{th}$, then V=0 and/or E=0; if $B_{enh}<B_{th}$, V=0 and/or E=0). The thresholds may be any value, such as about 48 or 64 on a scale of 0-255 for the $Edge_{th}$ and 96 or 64 for $B_{th}$. The thresholds identify spatial locations with sufficiently strong B-mode information to indicate tissue rather than fluid. Other processes with or without B-mode processing may be used to reduce bleed.

In another embodiment, holes in flow information are filled. Values of the ultrasound data representing flow that are below a display threshold are increased to values above the display threshold for the flow region. Velocity (V) and energy (E) estimates that are non-zero and less than the display threshold ($display_{th}$) are weighted or replaced. For example, if $0<abs(V)<display_{th}$, $V=sign(V)*display_{th}$, and if $0<E<display_{th}$ then $E=display_{th}$. The display threshold for the velocity is the same or different than for energy, and may be any value, such as 8-12 for a scale of 0-255. Since velocity is directional with positive and negative portions of the scale, a lower threshold may be used. Where flow is determined not to exist, such as where velocity and/or energy are set to 0, fill is not provided.

In another embodiment, flash in the ultrasound data representing flow is suppressed. The suppression is a function of B-mode information, but may be performed without B-mode information in other embodiments. Any suppression may be used. For example, in a current frame (N), V and E estimates are modulated with the B-mode values as: $E1=E(N)*(1-\gamma*(B_{enh}(N)+B_{enh}(N-1)))$ and $V1=V(N)*(1-\gamma*(B_{enh}(N)+B_{enh}(N-1)))$ where $\gamma$ is a fraction between 0 and 1/510 for a B-mode range of 0-511. The modulated V1 and E1 estimates are compared with a display threshold to determine locations without flow. If $E1<display_{th}$, then E=0, and if $V1<display_{th}$, then V=0. The display threshold is 8-12 for a range of 0-255 values, but may be another number. After thresholding, the remaining E and V values are persisted as a function of the B-mode information. For example, $V(N)=(1-\alpha(N))*V(N)+\alpha(N)*V(N-1)$ and $E(N)=(1-\alpha(N))*E(N)+\alpha(N)*E(N-1)$ where $\alpha(N)=(1-\beta)*B_{enh}(N)/255+\beta*B_{enh}(N-1)/255$ and $\beta$ is a fraction between 0 and 1, such as ½. Other persistence or modulations may be used. Infinite impulse response is used in this example, but finite impulse response processes may be performed.

The ultrasound data representing flow may be processed according to other processes. Combinations of two or more processes may be performed, such as reducing bleed, filling and flash suppression being performed sequentially on velocity and energy data.

The ultrasound data representing the region is used to determine orientation. In one embodiment, the flow data representing an area or volume is used, such as all of the flow information for a region. In other embodiments, the ultrasound data is decimated. Any amount of decimation may be used, such as using every second, third or fourth data point or spatial location. More than one decimation operation may be used, such as generating two frames of data associated with a same or different amount of decimation. For a same amount of decimation, the different frames may correspond to different starting locations for decimation. The ultrasound data representing flow is decimated, but ultrasound data representing tissue may be decimated. The decimation is provided with or without filtering.

In act 14, locations associated with flow are determined. In one embodiment, the processes used for reducing bleed, flash suppression, and/or filling define locations associated with flow. In another embodiment, additional or different thresholding is applied to determine locations associated with a desired level of flow. Energy, velocity, variance or combinations thereof may be thresholded. In other embodiments, display thresholds, automatic border detection, a region of interest, or user tracing define, at least in part, locations associated with flow.

The locations rather than the values are selected for determining orientation. For example, a binary image is generated. A 1 value represents spatial locations associated with flow, and a 0 value represents other locations (or vice versa). Other indications of location, such as a table of coordinates, may be used.

The orientation identification is based on flow locations, rather than B-mode information. Alternatively, B-mode information is used to determine, at least in part, the orientation.

An orientation of a tissue structure or flow region is determined in act 16. For example, the orientation of the Carotid artery, thyroid, kidney, liver, heart, vessel, or other structure is determined. The orientation corresponds to the flow or tissue. For example, locations associated with flow are used to determine an orientation of the flow. The orientation of flow provides or is the same as the orientation of the associated organ or tissue structure.

The orientation is determined as a function of the locations. The orientation is directly based on the locations, not on the values at the locations. Indirectly, the values are used to determine the locations. However, the locations without value information are used to determine the orientation. In alternative embodiments, the values are also used to determine the orientation.

The orientation is determined from the locations by area or volume based processing. For example, the binary image of locations is used to determine the orientation. Any now known or later developed area or volume based processing may be used. For example, a regional or local center of mass is determined with or without region shrinking.

In one embodiment represented by act 18, region shrinking is performed. The region shrinking or other area-based method generates or identifies a line representing or following the local or regional center of mass. The region shrinking is a function of the locations or of ultrasound data representing flow. For example, the binary image or other location representation is shrunk. Any region shrinking may be used, such as removing outer layers to define an internal line. For example, a morphological skeleton operation reduces area or volume objects to lines. A kernel is applied to the locations. Any size kernel may be used, such as a 3×3, other symmetric or asymmetric kernel. The kernel is applied to non-overlapping portions of the binary image. For each kernel location, a median is determined. All of the data (e.g., 9 locations for a 3×3 kernel) for a given kernel location is replaced by the median. The morphological skeleton operation is iteratively repeated by repeating the process a plurality of times. Eventually, the region does not converge any further or reaches a threshold number of iterations or amount of region shrinking. The result is a line or region having a direction. The line is straight or curved. More than one line may result, such as lines with branches and/or associated with different regions.

If two or more frames of data associated with different decimation are provided, skeletons or lines are determined separately for each frame. Skeletons or lines not present from all or some of the frames are rejected, and lines present in some or all of the frames are maintained. Small color regions that can distort the skeleton orientations may be removed by rejection of the skeletons. The region shrinking process may or may not be repeated after removal of the rejected lines and corresponding flow information.

Figure 2:
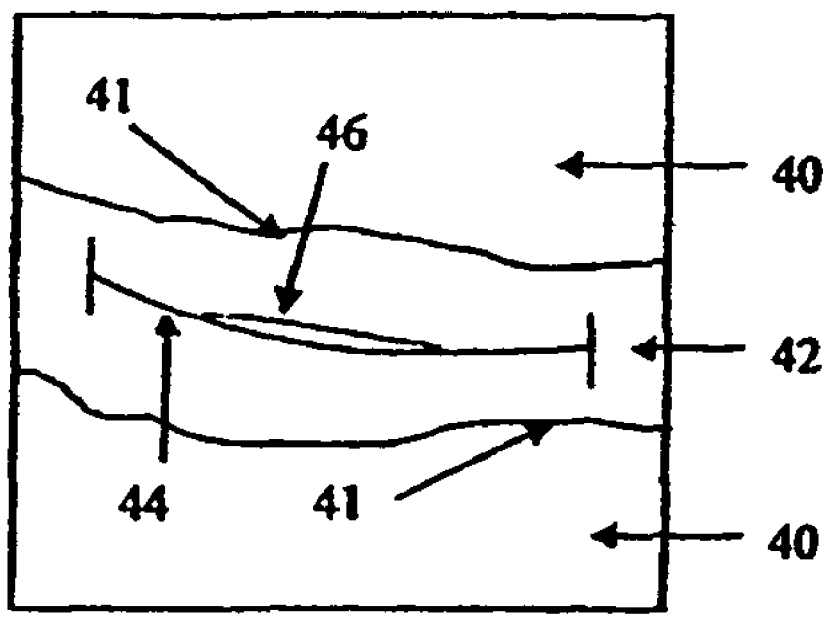
FIG. 2 is a graphical representation of one embodiment of a region associated with flow.

FIG. 2 shows a two-dimensional image of a vessel with an associated flow region 42 having vessel walls 41. Tissue 40 is around the flow region 42. The binary image provides for flow locations within the flow region 42 and not within the tissue 40. The flow region 42 is shrunk to identify the line 44.

In act 20, a flow direction is determined as a function of the region shrinking. For example, the line 44 is determined from the convergence of the region shrinking. This skeletal line 44 from the output of the morphological skeleton operation indicates a direction of flow.

In other embodiments, the line is filtered or processed to determine the flow direction. For example, a straight line 46 associated with the entirety of or a portion of the skeleton line 44 is determined. The straight line 46 may be an average slope of the skeleton line 44. As another example, a Hough or Radon transform is applied to the skeleton line 44 to identify the slope and location of the straight line 46 with the highest energy. Any kernel size may be used, such as an 8×8 kernel. Alternatively, a piecewise line-fit is performed on the skeleton line 44 to identify orientation. Each line 44 is treated separately for line fitting. Alternatively, a bank of filters with specific orientations is used for identifying the orientation of small (e.g., 8×8 or 4×4) regions in the skeletal image. By filtering for different orientations, one of the oriented filters identifies the straight line 46 and other filters filter out the skeleton line 44. Other processes or filtering may be used.

More than one skeleton line 44 may exist, such as for images of an organ or other structure with branching or different flow regions. One or more of the skeleton lines 44 or other lines 46 are selected. Any selection criteria may be used, such as manual input, longest line, straightest line, or line closest to a center of an image. For example, the skeletal line 44 associated with a greatest number of flow locations is selected. The number of pixels or locations rejected or replaced during region shrinking indicates a number of flow locations associated with a given line 44. The locations included in the count are contiguous with the skeletal line 44. The skeletal line 44 that corresponds to the largest color region within an image is selected.

The selected skeletal line 44 or a corresponding processed line 46 (e.g., a straight line) indicate the orientation of the flow, flow region, and/or associated tissue structure. The orientation may or may not be displayed to the user. The orientation may or may not be used for further processing and/or to set imaging parameters. Acts 22, 24, 26, and 28 correspond to further processes using the orientation.

In act 22, a spectral Doppler gate is positioned as a function of the orientation. The center location, width, and/or orientation of the gate are positioned based on the orientation. The spectral Doppler window is positioned at an ultrasound scan line that is closest to the central pixel of the skeletal line 44 or closest to an intersection of the skeletal line 44 with a particular location or other line. The window may be oriented along the same orientation as the skeletal line 44. Perpendicular to the skeletal line 44, the extent of the flow region is determined. The perpendicular extent or distance is determined from the center location of the gate. The width of the gate is set to or less than the distance. The length of the gate is set automatically to assure that the entire gate is within the flow region. Any reasonable window size for spectral Doppler that does not exceed the extent of the flow region at a given location may be used.

In act 24, a scan line angle is set as a function of the orientation. The scan lines for color or flow imaging may be oriented to be more along the direction of flow. The orientation, such as the mean orientation within a region of interest, is determined. A steering angle or angles available with a given transducer at a given position on the patient are selected. The angle is selected to match, to the extent possible, the mean orientation. The scan lines are as parallel as possible to the orientation so that the velocity determined by Doppler or flow processing more closely matches the actual velocity. B-mode scan lines may be positioned to be as perpendicular as possible. Tissue structures may more strongly reflect acoustic energy with a perpendicular relationship. Scan lines for B-mode, flow mode, or both may be adjusted or set as a function of the orientation.

In act 26, the velocity values are corrected or altered as a function of the orientation. For example, a lateral flow velocity is determined as a function of the orientation. The velocity values represent velocity along a scan line. The scan lines may not be parallel with the flow direction. The magnitude of velocity along the flow direction is different than the detected velocity. The detected velocity may include both lateral and axial flow information to different extents. For each velocity along a given ultrasound line, a corresponding closest skeletal line location is determined. The orientation of the skeletal line locations relative to the scan line is determined. This angle information allows determination of the component of the velocity along the vessel wall ($V_{wall}$) or flow direction. The velocity is corrected based on the orientation of the skeletal pixel with respect to the ultrasound line as: $V_{wall}(i,j)=V(i,j)/\cos\theta(i,j)$. Other angle corrections may be used, such as to identify turbulent flow in directions other than the flow direction.

As another example of correction of velocity values, a sign of the lateral flow velocity, an axial flow velocity, or another velocity is corrected. Due to curvature of the flow region and/or orientation of the scan lines through the flow region, some portions of the region may show negative flow and other portions positive flow where all of the portions should be positive or negative. The aliasing of the velocity is corrected as a function of a line 44 associated with the orientation. The mean or median sign ($S_{mean}$) of the velocities for locations along the skeletal line 44 is determined. For velocities within the flow region whose sign does not match $S_{mean}$, the sign is corrected. A local neighborhood (e.g., 3×3) may be filtered to correct the magnitude of the axial and lateral velocities.

Both sign and angle correction may be performed. One or the other may be performed. Other velocity corrections may be performed.

In act 28, other image enhancements are performed as a function of the orientation. B-mode and/or flow mode (e.g., velocity or energy) images are enhanced. For example, the orientation is compared to an orientation derived from a B-mode image. Tissue edges are determined as a function of B-mode information. Boundary detection may be used. In one embodiment, the B-mode edge image determined as discussed above for bleeding reduction is used. The edge image is or is not decimated. Any number of decimation frames may be generated, such as one or two levels. Using locations, area or volume based processing determines lines associated with edges. A morphological skeleton operation is performed on the decimated or entire B-mode edge image ($B_{edge}$). For example, region shrinking of a binary B-mode edge image provides B-mode edge locations. The B-mode edge locations are compared with the color pixel coordinates to reduce color bleed. Other edge detection may be used.

Tissue edges associated with the tissue structure or flow orientation are selected. The edge orientation and location are compared with the flow orientation to identify vessel walls in the B-mode image. If the coordinates of a flow skeleton line 44 lie within the coordinates of two B-mode edges, then the B-mode edges represent the vessel walls or tissue regions associated with vessel walls defined by the extent of the flow region.

The B-mode information may be filtered as a function of the selected tissue edges. Filtering may make the B-mode edges more continuous and smooth along vessel walls. A directional low-pass filter, such as with a 3×3 kernel whose coefficients are strong along the vessel orientation, may highlight the tissue edges. For regions in the B-mode image that do not contain strong edges, a symmetric smoothing kernel may reduce speckle.

As an alternative or in addition to filtering based on the tissue edges, the demodulation frequency, depth-gain curve or both are set as a function of the selected tissue edges. The demodulation frequencies and the depth-gain compensation (dgc) curves are modified according to the location and size of the flow region. The attenuation caused by tissue is different than caused by flow. The demodulation frequency and depth-gain curve may account, at least in part, for the different attenuation. By using the orientation information, the extent of the flow region and the tissue regions is determined. Modifying for different attenuation may improve the B-mode registration and image quality over depth. For example, the location and number of breakpoints for demodulation frequencies and depth-gain curve can be varied dynamically.

As another example of act 28, the flow image is enhanced by artifact reduction. The flow is enhanced as a function of B-mode images, such as an enhanced B-mode image as discussed above or another B-mode image. The velocity data is altered as a function of the selected tissue edges and the orientation of the flow region. The B-mode edge orientations are compared with the color orientations to identify the extent of the flow region. If coordinates of a flow orientation line lie within the coordinates of two B-mode edges, the flow orientation is part of a flow region. Other flow orientations may be discarded. For each flow region, aliasing is reduced using the vessel orientation and the flow direction. Filling or reduction of holes in the flow is performed using local spatial filtering or correcting/re-estimating velocities in the holes using the flow direction information.

Figure 3:
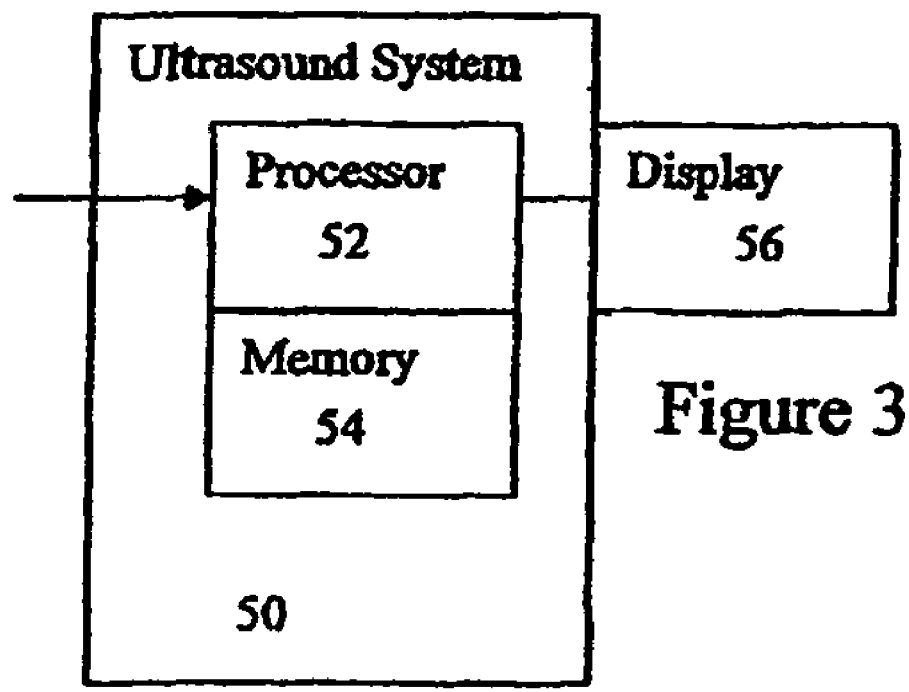
FIG. 3 is a block diagram of one embodiment of a system for automatic identification of orientation in medical diagnostic ultrasound.

FIG. 3 shows a system 50 for automatic identification of orientation in medical diagnostic ultrasound. The system 50 is a medical diagnostic ultrasound imaging system, but may be a computer, workstation, database, server or other system. The system 50 includes a processor 52, a memory 54, and a display 56. Additional, different, or fewer components may be provided.

The memory 54 is a buffer, cache, RAM, removeable media, hard drive, magnetic, optical, or other now known or later developed memory. The memory 54 is a single device or group of two or more devices.

The memory 54 stores the ultrasound data. For example, the memory 54 stores flow (e.g., velocity, energy or both) and/or B-mode data. Alternatively, the ultrasound data is transferred to the processor 52 from another device.

The memory 54 is additionally or alternatively a computer readable storage medium with processing instructions. Data representing instructions executable by the programmed processor 54 for automatic identification of orientation in medical diagnostic ultrasound is stored in the memory 54. The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, filmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The processor 52 is a general processor, digital signal processor, application specific integrated circuit, field programmable gate array, digital circuit, analog circuit or other now known or later developed device for processing ultrasound data. The processor 52 is a single device, a plurality of devices, or a network. For more than one device, parallel or sequential division of processing may be used.

The processor 52 is operable to perform one or more of the acts discussed above. For example, the processor 52 applies area or volume based processing to ultrasound data, such as flow and/or tissue data. The processor 52 identifies a line as a function of the area or volume based process and free of a determination of a location of maximum velocity, energy or both. For example, the line is determined from locations rather than flow values. The orientation may be used for any purpose. For example, the processor 52 alters B-mode information as a function of the orientation or line associated with a flow region. As another example, the processor 52 alters ultrasound data as a function of B-mode edges.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for automatic identification of orientation in medical diagnostic ultrasound, the method comprising:
 obtaining ultrasound data representing a multi-dimensional region bounded by a tissue structure;
 determining locations associated with the multi-dimensional region as a function of the ultrasound data; and
 determining an orientation of the tissue structure as a function of the locations;
 wherein determining the orientation comprises iteratively performing a morphological skeleton operation on the locations, a skeletal line being an output of the performing of a last of the iterations such that a result of the last iteration, without further processing, of the morphological skeleton operation is an internal line of the multi-dimensional region, the multi-dimensional region shrunk down to the internal line by the morphological skeleton operation, the internal line being thinner along a length of the internal line than regions of flow on each of opposite sides of the internal line, the regions of flow within the multi-dimensional region bounded by the tissue structure, the regions of flow being areas thicker than the internal line along the length of the internal line such that the internal line is spaced away from the bounding tissue structure along the entire length by the regions of flow.

2. The method of claim 1 wherein the ultrasound data represents flow and wherein obtaining comprises:
 performing:
  suppressing bleed of the ultrasound data representing flow onto locations associated with tissue boundaries as a function of B-mode information;
  increasing values of the ultrasound data representing flow below a display threshold to values above the display threshold
  suppressing flash in the ultrasound data representing flow, the suppressing being a function of B-mode information; or
  combinations thereof.

3. The method of claim 1 wherein determining locations comprises generating a binary image as a function of a threshold applied to the ultrasound data, and wherein determining the orientation comprises area or volume based processing of the binary image.

4. The method of claim 1 wherein obtaining comprises decimating the ultrasound data, the determining the locations and determining the orientations based on the decimated ultrasound data.

5. The method of claim 1 wherein determining the orientation comprises region shrinking as a function of the locations.

6. The method of claim 1 further comprising:
 selecting the skeletal line from a plurality of lines as a function of a number of the locations associated with each of the plurality of lines; and
 identifying a straight line as a function of the selected skeletal line.

7. The method of claim 1 further comprising:
 positioning a spectral Doppler gate as a function of the orientation.

8. The method of claim 1 further comprising:
 setting a scan line angle as a function of the orientation.

9. The method of claim 1 further comprising:
 performing:
  determining a lateral flow velocity as a function of the orientation;
  correcting a sign of the lateral flow velocity, an axial flow velocity, or another velocity as a function of a line associated with the orientation; or
  combinations thereof.

10. The method of claim 1 wherein determining the orientation comprises determining tissue edges as a function of B-mode information;
 further comprising:
 selecting tissue edges associated with the tissue structure; and
 filtering the B-mode information as a function of the selected tissue edges.

11. The method of claim 1 wherein determining the orientation comprises determining tissue edges as a function of B-mode information;
 further comprising:
 selecting tissue edges associated with the tissue structure; and
 setting demodulation frequency, depth-gain curve or both as a function of the tissue edges.

12. The method of claim 1 further comprising:
 determining tissue edges as a function of B-mode information;
 selecting tissue edges associated with the tissue structure; and
 altering the velocity data as a function of the selected tissue edges and the orientation.

13. The method of claim 1 wherein determining the orientation comprises locating a regional center of mass.

14. The method of claim 1 further comprising:
 identifying a largest flow region.

15. In a non-transitory computer readable storage medium having stored therein data representing instructions executable by a programmed processor for automatic identification of orientation in medical diagnostic ultrasound, the storage medium comprising instructions for:
 obtaining ultrasound data representing a multidimensional region;
 region shrinking the multidimensional region to a line as a function of the ultrasound data such that the line directly results from a convergence of the region shrinking, the line being a geometric line corresponding to a point extending along a curve; and
 determining a direction as a function of the region shrinking wherein determining the direction comprises determining from the line.

16. The non-transitory computer readable storage medium of claim 15, wherein the instructions further comprising generating a binary image as a function of a threshold applied to the ultrasound data, wherein region shrinking comprises region shrinking the binary image.

17. The non-transitory computer readable storage medium of claim 15, wherein the instructions wherein region shrinking comprises iteratively performing a morphological skeleton operation on the region, and wherein determining the flow direction comprises identifying a skeletal line from the output of the morphological skeleton operation.

18. The non-transitory computer readable storage medium of claim 15, wherein the instructions wherein the ultrasound data represents flow and the direction is a flow direction; further comprising performing:
positioning a spectral Doppler gate as a function of the flow direction;
setting a scan line angle as a function of the flow direction;
determining a lateral flow velocity as a function of the flow direction;
correcting a sign of the lateral flow velocity, an axial flow velocity, or another velocity as a function of a line associated with the flow direction; or
combinations thereof.

19. The non-transitory computer readable storage medium of claim 15, wherein the instructions wherein determining a direction comprises determining tissue edges as a function of B-mode information; further comprising:
selecting tissue edges associated with the region; and
filtering the B-mode information as a function of the selected tissue edges.

20. The non-transitory computer readable storage medium of claim 15, wherein the instructions further comprising:
determining tissue edges as a function of B-mode information;
selecting tissue edges associated with the region; and
performing:
setting demodulation frequency, depth-gain curve or both as a function of the tissue edges;
altering velocity data as a function of the selected tissue edges and the flow direction; or
combinations thereof.

* * * * *